(12) United States Patent
Jackson

(10) Patent No.: US 6,821,298 B1
(45) Date of Patent: *Nov. 23, 2004

(54) ANTERIOR EXPANDABLE SPINAL FUSION CAGE SYSTEM

(76) Inventor: Roger P. Jackson, 6600 Indian La., Mission Hills, KS (US) 66208

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/552,743

(22) Filed: Apr. 18, 2000

(51) Int. Cl.[7] ................................................. A61F 2/44
(52) U.S. Cl. ................................. 623/17.15; 623/17.11
(58) Field of Search ......................... 623/17.11, 17.15, 623/17.16; 606/61

(56) References Cited

U.S. PATENT DOCUMENTS

| | | | |
|---|---|---|---|
| 4,863,476 A | 9/1989 | Shepperd | |
| 5,015,255 A | 5/1991 | Kuslich | |
| 5,055,104 A | 10/1991 | Ray | |
| 5,059,193 A | 10/1991 | Kuslich | |
| 5,228,083 A * | 7/1993 | Lozowick et al. | 713/160 |
| 5,263,953 A | 11/1993 | Bagby | |
| 5,458,638 A | 10/1995 | Kuslich et al. | |
| 5,489,307 A | 2/1996 | Kuslich et al. | |
| 5,489,308 A | 2/1996 | Kuslich et al. | |
| 5,554,191 A | 9/1996 | Lahille et al. | |
| 5,593,409 A | 1/1997 | Michelson | |
| 5,609,636 A | 3/1997 | Kohrs et al. | |
| 5,653,763 A | 8/1997 | Errico | |
| 5,658,336 A * | 8/1997 | Pisharodi | 623/17.16 |
| 5,658,337 A | 8/1997 | Kohrs et al. | |
| 5,665,122 A | 9/1997 | Kambin | |
| 5,669,909 A | 9/1997 | Zdeblick et al. | |
| 5,683,391 A | 11/1997 | Boyd | |
| 5,693,100 A * | 12/1997 | Pisharodi | 623/17.16 |
| 5,702,453 A | 12/1997 | Rabbe et al. | |
| 5,776,197 A | 7/1998 | Rabbe et al. | |
| 5,776,198 A | 7/1998 | Rabbe et al. | |
| 5,782,919 A | 7/1998 | Zdeblick et al. | |
| 5,797,909 A | 8/1998 | Michelson | |
| 5,865,847 A | 2/1999 | Kohrs | |
| 5,885,287 A | 3/1999 | Bagby | |
| 5,980,522 A * | 11/1999 | Koros et al. | 606/61 |
| 6,102,950 A * | 8/2000 | Vaccaro | 606/61 |
| 6,117,174 A * | 9/2000 | Nolan | 623/17.11 |
| 6,129,763 A * | 10/2000 | Chauvin et al. | 623/17.11 |
| 6,176,882 B1 * | 1/2001 | Biedermann et al. | 623/17.15 |
| 6,438,592 B1 * | 8/2002 | Killian | 709/224 |

FOREIGN PATENT DOCUMENTS

WO      WO-9907312 A1 *   2/1999   ............. A61F/2/44

* cited by examiner

*Primary Examiner*—Brian E Pellegrino
(74) *Attorney, Agent, or Firm*—John C. McMahon

(57) ABSTRACT

A fenestrated, hollow intervertebral cage containing a packed, harvested bone graft for fusing adjacent vertebrae together while maintaining or correcting the angular alignment and balance of the spine. Use of the device for an anterior interbody fusion results in a fused bone segment having a predetermined fixed angular orientation. The apparatus has a cage unit adjustably coupled to an expansion cap, and an adjustable wedge to support the adjacent vertebrae with facing surfaces at a predetermined angle relative to each other. A connecting bolt may be threaded or fixed to the rear of the cage unit. In certain embodiments, the cage unit and expansion cap are interlocking. Also in certain embodiments, especially utilizing round cages, the expansion cap may also include upper and lower horizontal bone-supporting surfaces and an anterior recess for receiving fasteners. A pair of independently adjustable cage units can be fixedly intercoupled by a link.

8 Claims, 9 Drawing Sheets

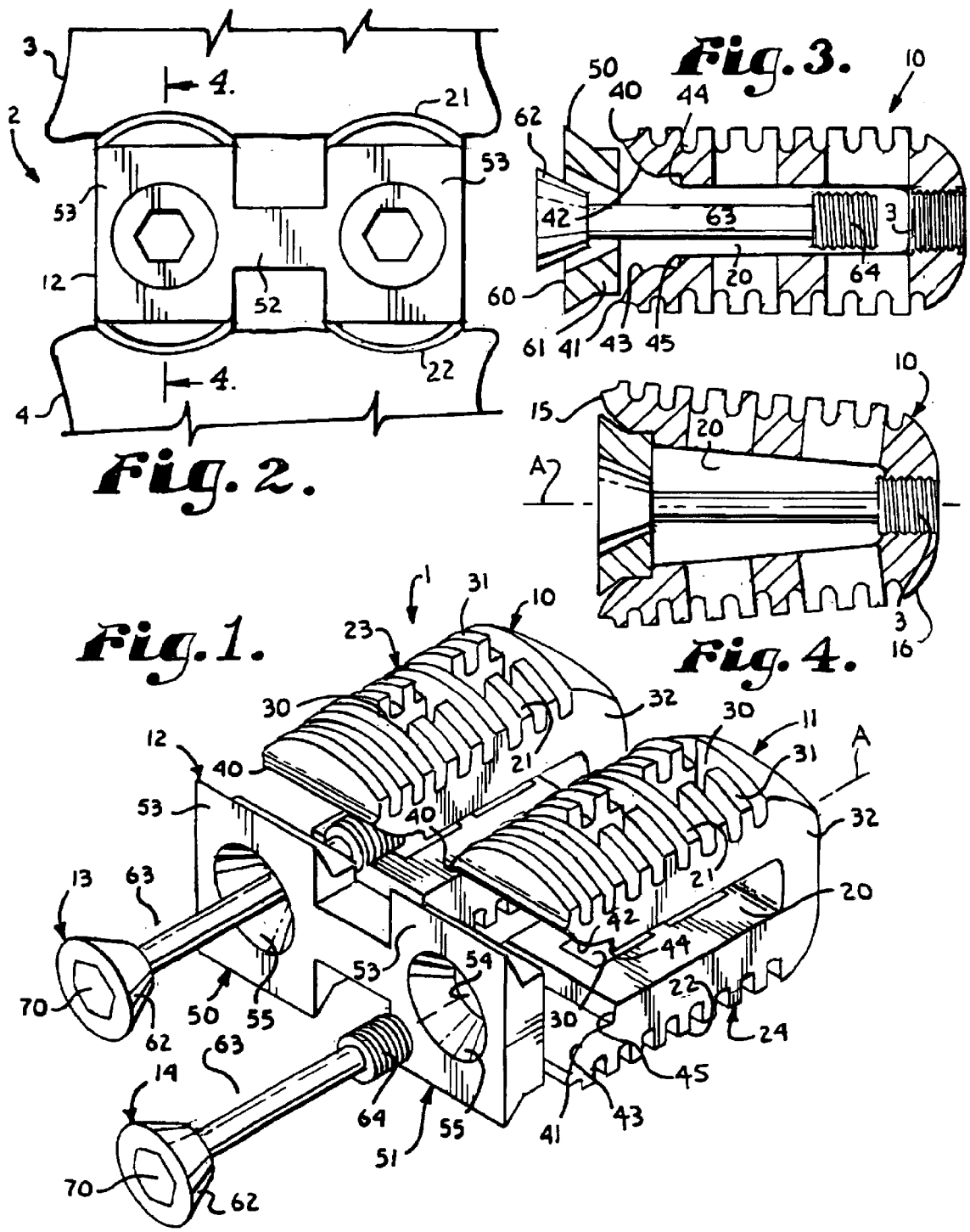

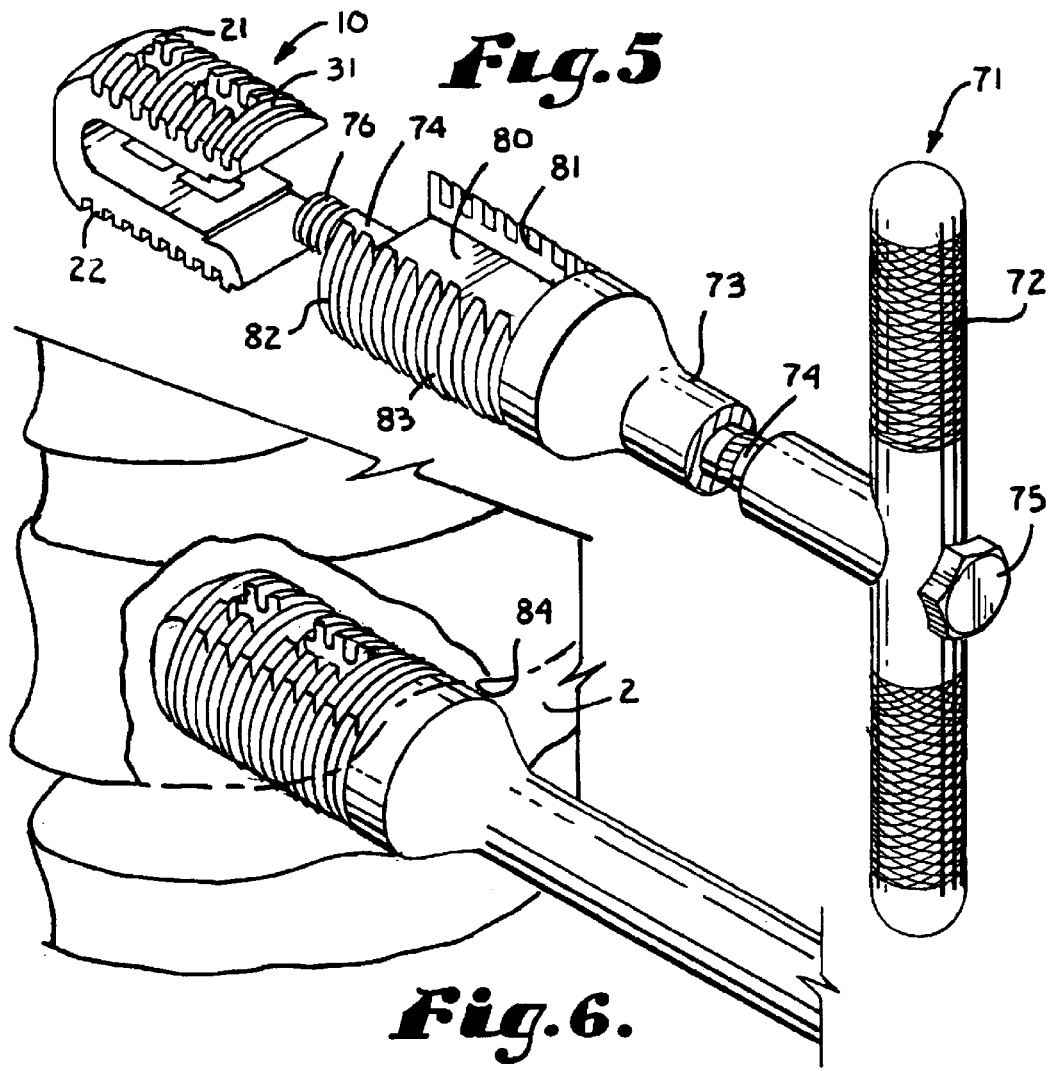
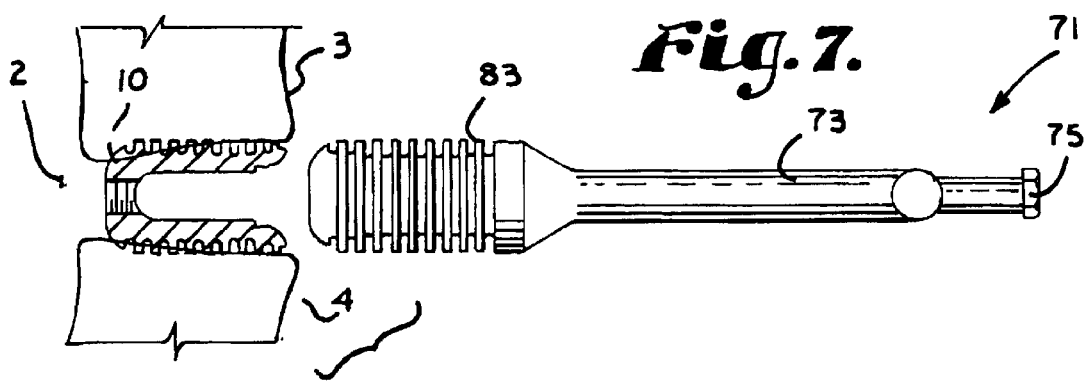

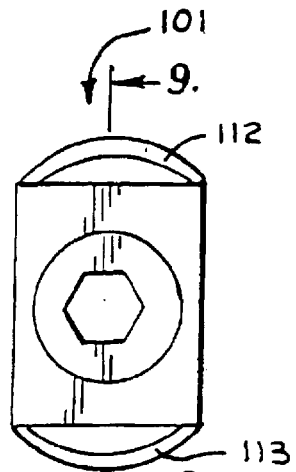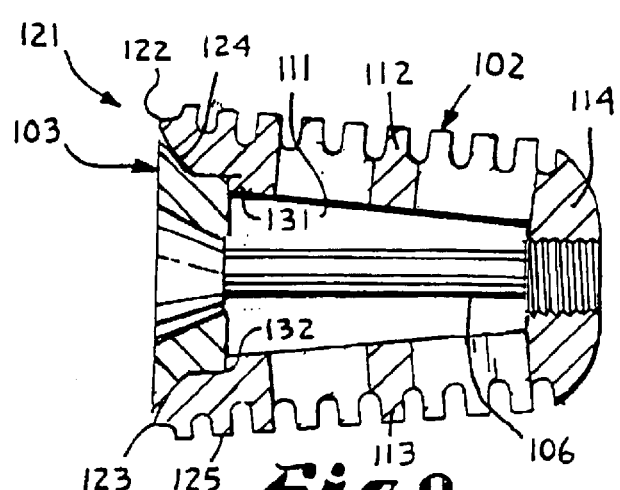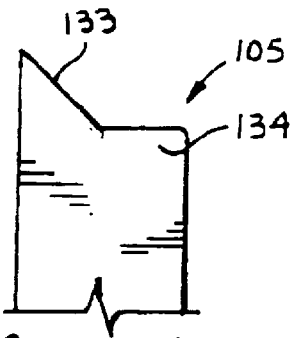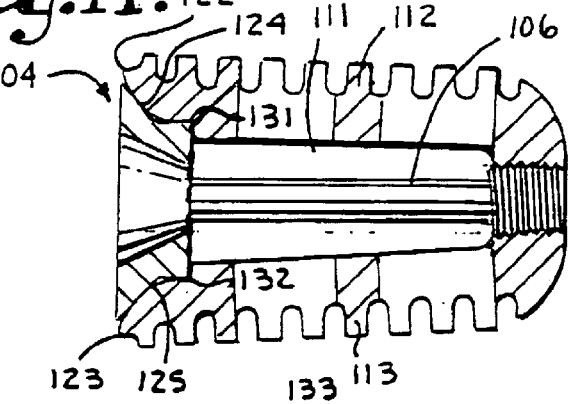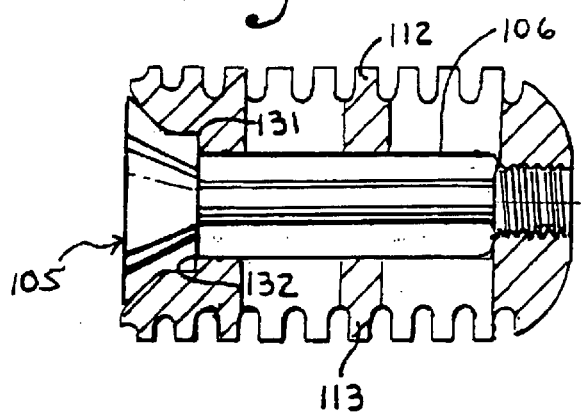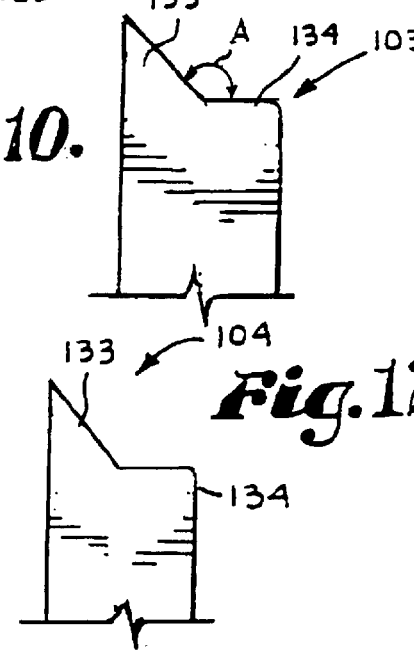

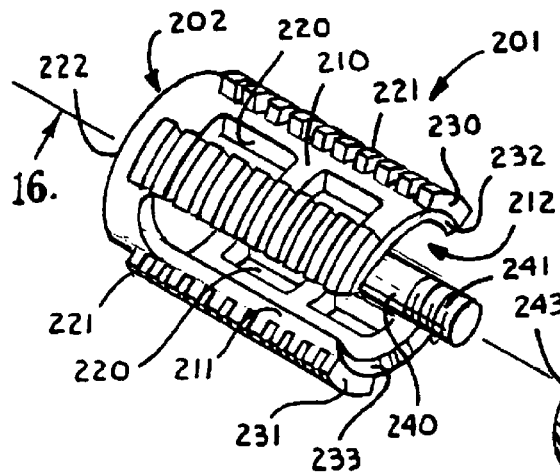
*Fig.15.*
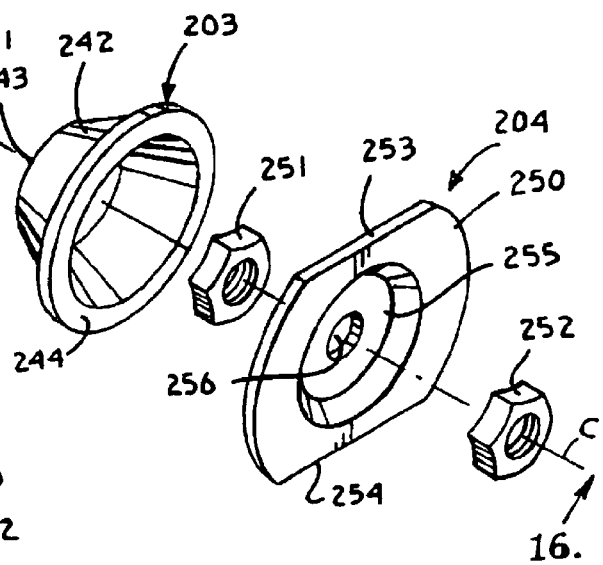
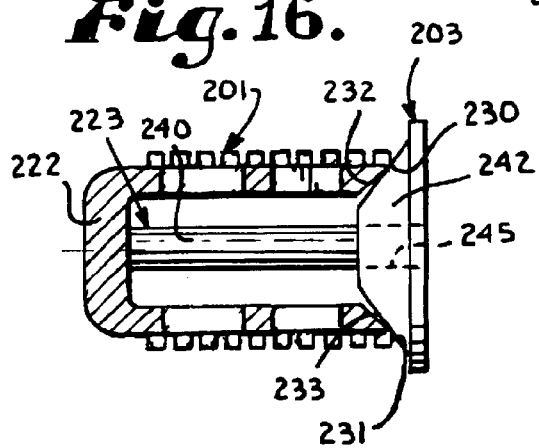
*Fig.16.*
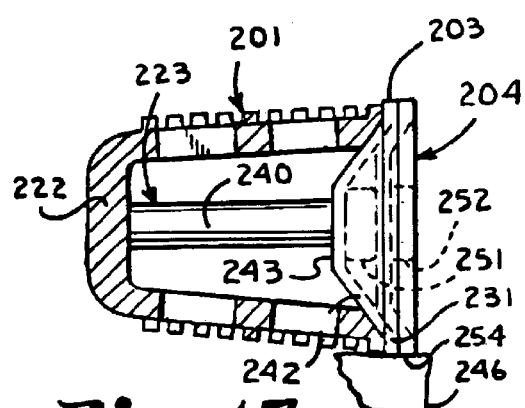
*Fig.17.*

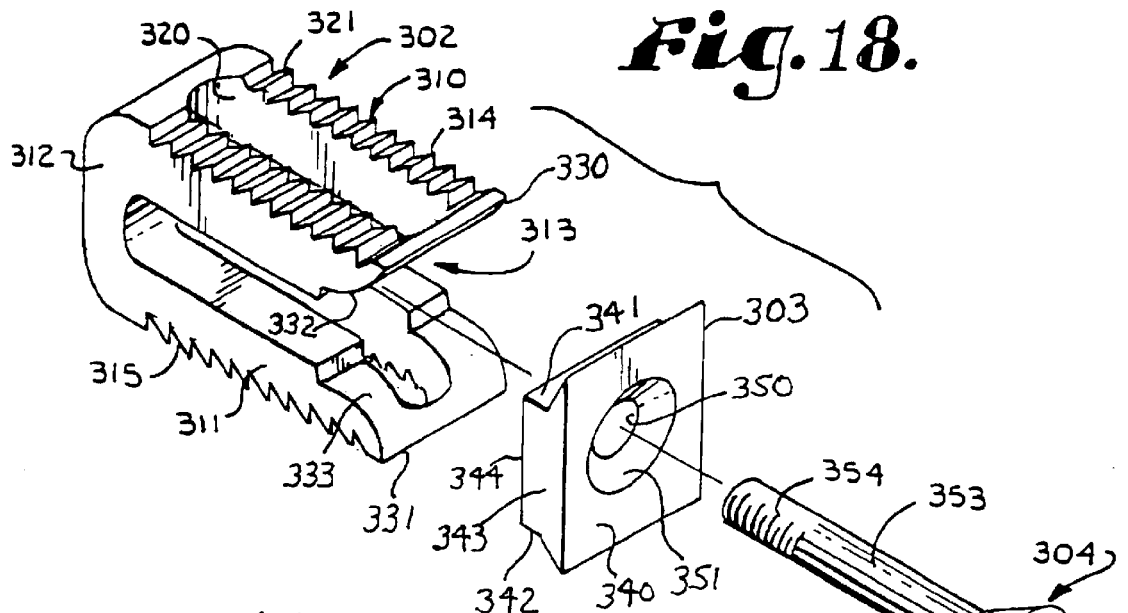
Fig. 18.
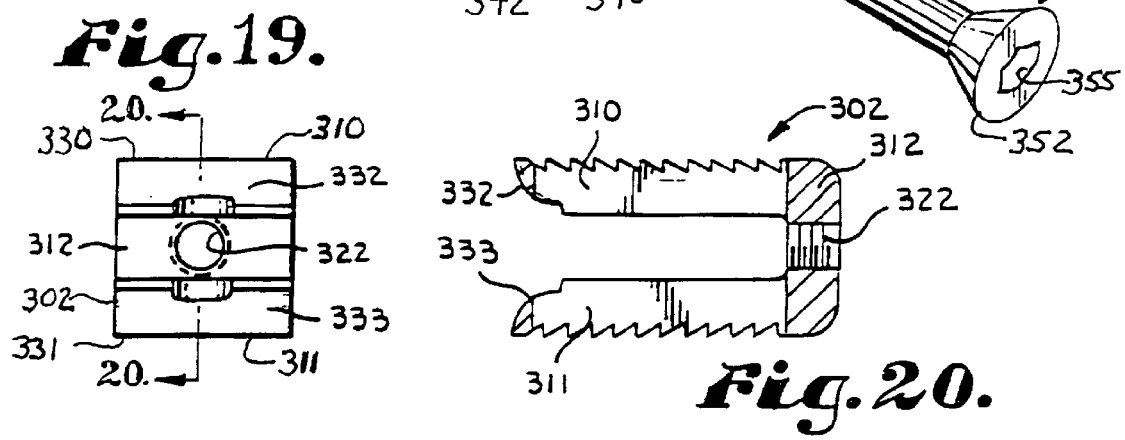
Fig. 19.
Fig. 20.
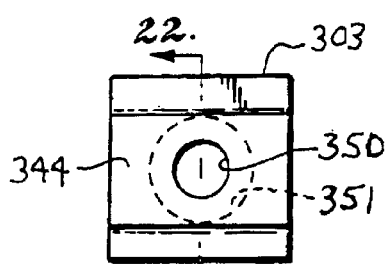
Fig. 21.
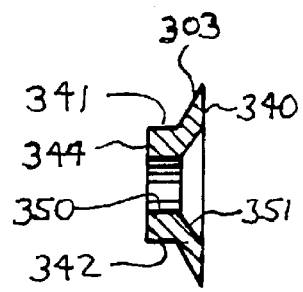
Fig. 22.

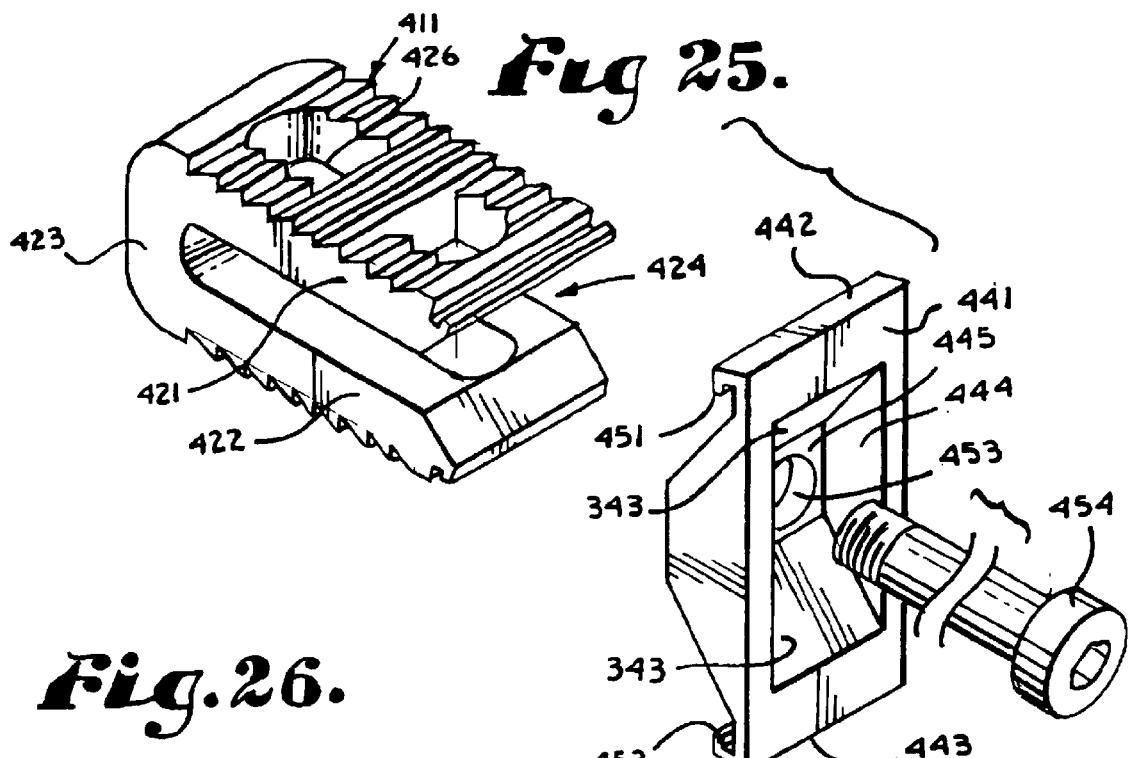
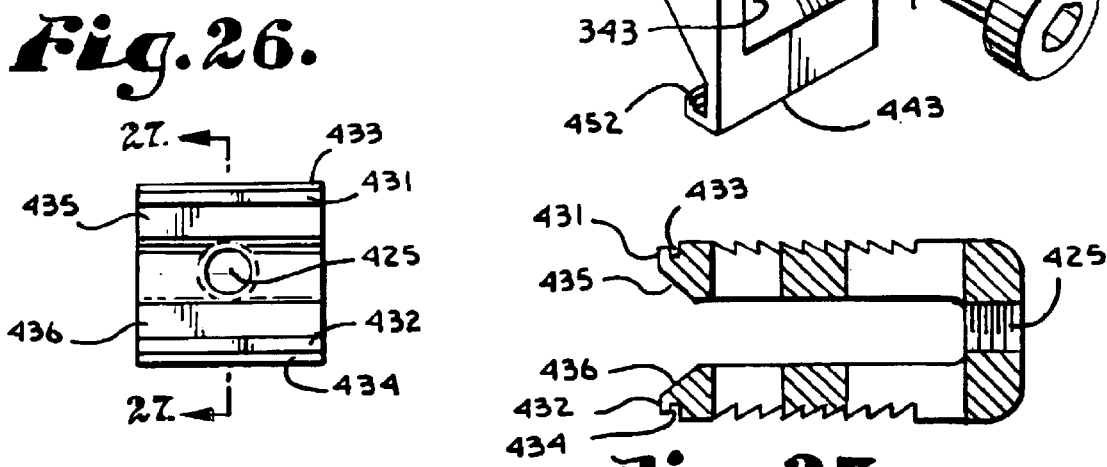
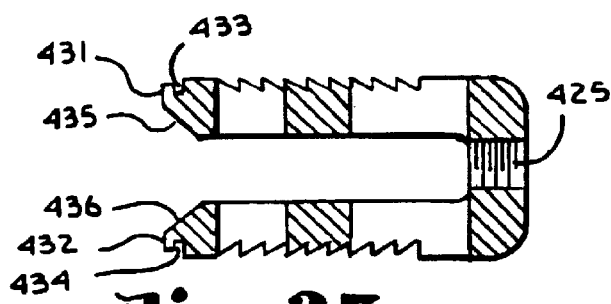
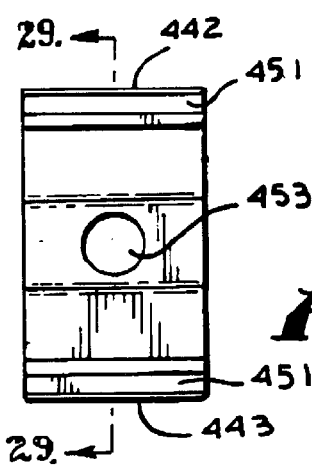
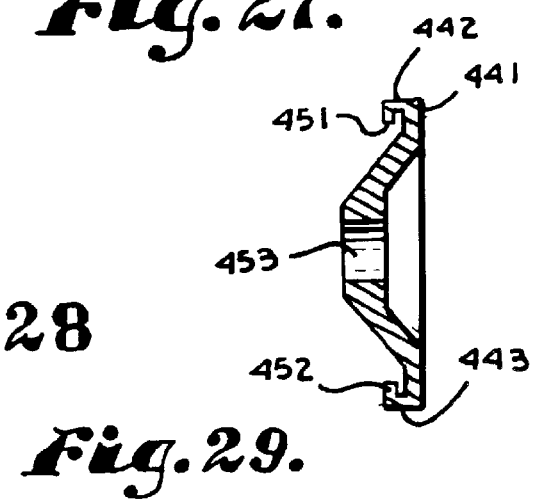

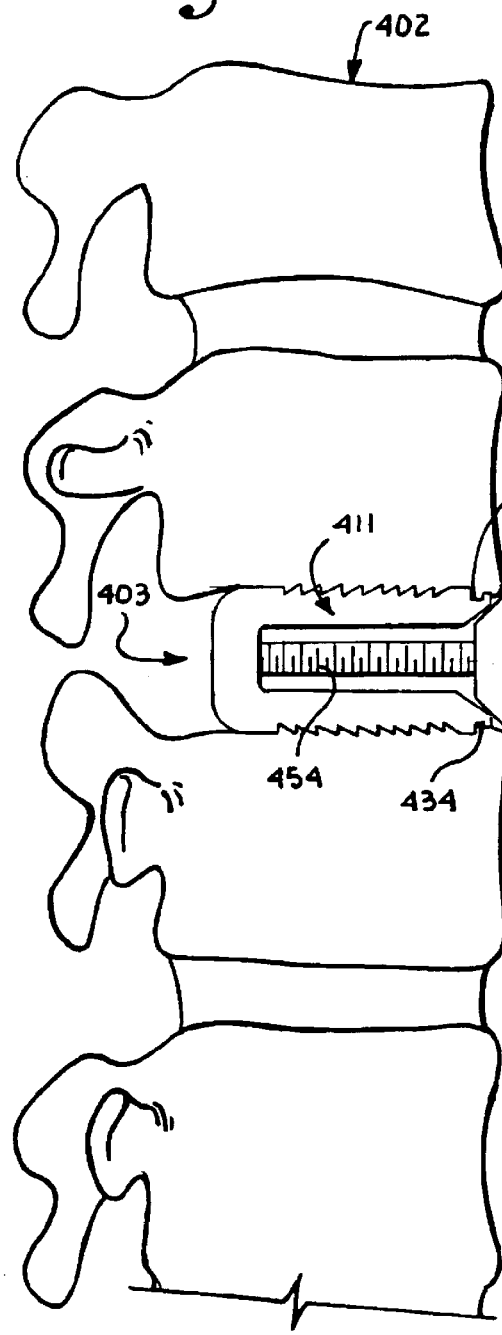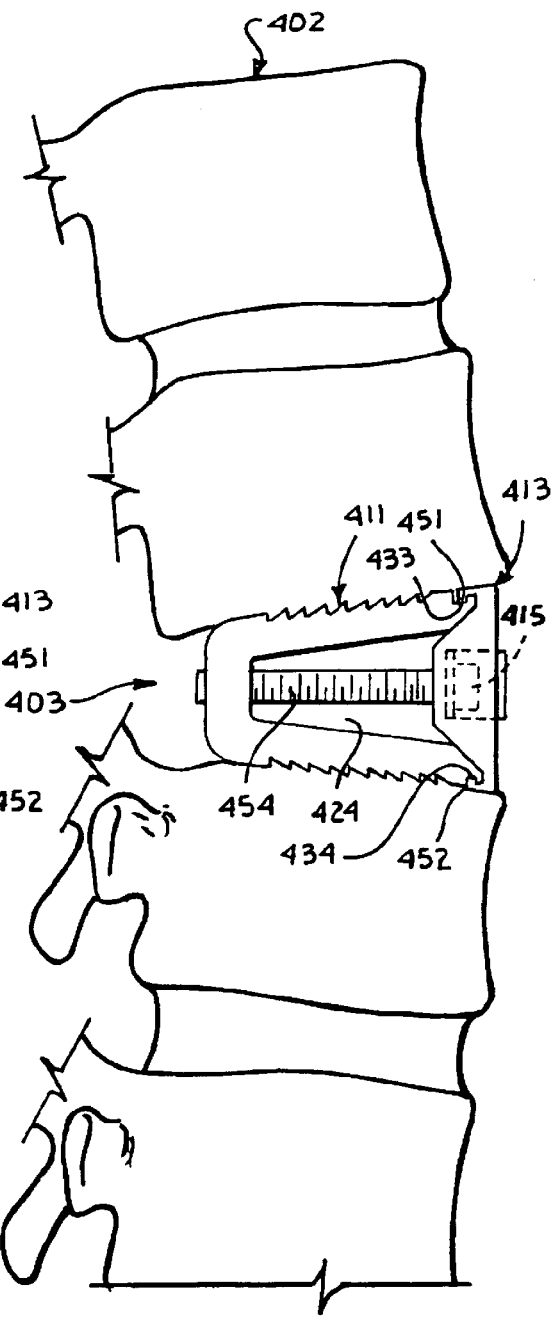

ANTERIOR EXPANDABLE SPINAL FUSION CAGE SYSTEM

BACKGROUND OF THE INVENTION

The present invention is generally directed to an apparatus and method for implanting an anterior installed intervertebral fusion cage system which can be selectively expanded anteriorly between two adjacent vertebrae to cause them to change position relative to each other and produce a normal alignment of the spine, while promoting fusion of the vertebrae. More particularly, the invention discloses an apparatus and method for surgically positioning an implant having a fusion cage and one or more alternative expansion caps which may be intercoupled with the cage to cause expansion of the anterior portion of the cage to form an adjustable wedge for alignment of two adjacent vertebral bodies in accordance with a predetermined and desired spinal curvature.

The implant of the present invention preferably presents an anterior surface which is flush or slightly recessed within the intervertebral joint, so that it does not abrade or otherwise injure surrounding tissues. In certain embodiments the device further includes structure for supporting a substantial portion of the front of the implant against a layer of harder, more compact bone at the anterior surface of the vertebrae in order to reduce the likelihood of subsidence of the device into the bone. Adjacent cages between a pair of vertebrae are preferably linked transversely to provide additional stabilization of the vertebrae.

The spine is a column of stacked vertebrae, each having a rounded, anterior element, or vertebral body which is weight-bearing. The vertebral bodies are separated from each other and cushioned by a series of fibrocartilage pads or discs which impart flexibility to the spine. Aging, injury and disease, such as degenerative disc disease, may result in drying out or collapse of the discs, causing back and leg pain. In some cases the disc or vertebra is damaged beyond repair or must be removed for medical reasons.

While the spinal column appears to be straight when viewed from an anterior or posterior vantage point, when viewed laterally it is apparent that it is actually comprised of four curved regions. In some congenital conditions such as scoliosis and kyphosis, excessive curvature or other displacement of the spinal vertebrae of the spine occurs.

Treatment of weakness, injury or improper curvature by removal of a disc and fusion of adjacent vertebral bodies (arthrodesis) has become relatively commonplace in recent years. More than 20,000 such interbody fusions of the lumbar region alone are now performed annually in the United States. Fusion of adjacent vertebral bodies is generally accomplished by implantation of a cage-like device in the intervertebral space. The cages are apertured, and include a hollow interior chamber which is packed with live bone chips, usually harvested from the patient's hip, less frequently from the leg, spine or ribs, or bone may be obtained from a bone bank. A bone substitute may also be employed. Following implantation, bone from each of the adjacent vertebrae grows through the apertures to fuse with the bone of the other vertebrae above and below the cage, thus stabilizing the area. The fusion process may take six to twelve months and it is desirable to stabilize both the vertebrae and the cages during the fusion process.

Once the fusion cage has been inserted, the angular orientation of the top and bottom surface of each cage is of importance, because this orientation determines the fixed angular alignment of the facing surfaces of the two vertebrae upon fusion. The cervical and lumbar curves each present a region of normal anterior convexity and posterior concavity or physiological lordosis. There is a need for an implant which can be adjusted in situ to conform to and maintain lordosis of the segments involved in the fusion or adjusted to correct a preexisting deformity and to restore or initiate proper angular vertebral alignment along the spine.

Like most other bones, the bones of the spine and, in particular, the vertebral bodies, consist of a core of spongy, cancellous tissue surrounded by a rim of harder, more compact bone. One problem associated with the implantation of intervertebral fusion cages has been eventual subsidence of the cage into the softer or spongier bone that is normally on opposite sides of a disc following implant. However, there is an anterior crescent of harder bone close to the edge of the vertebral bodies. There is a need for an implant which can be installed to provide support along the full length of the upper and lower face of the implant cage, for positioning the cage against a substantial length of the harder, outer rim of bone to provide better anterior support.

Normally, a pair of fusion cage implant devices are inserted into the area previously occupied by a disc in spaced relationship to each other. In order to provide lateral stability, it is desirable to link the two cages together. There is a need for the cages to be adjustable in situ to preserve or restore coronal, axial and sagittal alignment. It is also preferable that the cages be linked by a structure which is recessed within the intervertebral joint. When the cages are inserted into the anterior portion of the intervertebral space, any structure which projects beyond the anterior surface of the vertebral body may cause irritation or damage to the surrounding tissues and vasculature, especially major arteries that are located close to the spine, or to the ligaments and muscles along the spine.

The apparatus and method of the present invention are specifically designed to provide both independent intervertebral implants and transversely linked pairs of implants, which can be selectively expanded anteriorly to conform the vertebrae to a desired angle of curvature of the affected spinal region while supporting the anterior margin of the adjacent vertebral bodies and to do so without abrading or damaging the surrounding tissues subsequent to insertion.

SUMMARY OF THE INVENTION

The present invention is directed to an apparatus and method for implanting an intervertebral cage containing a bone graft to allow for the fusing together of adjacent vertebrae, while maintaining or correcting the angular alignment of the spine. The invention provides an improved fusion cage that allows selective adjustment between adjacent vertebrae. The apparatus includes a pair of cage units that have tops and bottoms and are each adjustably coupled to an expansion cap, such that the top and bottom form a wedge which may be adjusted to support the adjacent vertebrae at a predetermined angle. The cage is formed of a resilient material and is generally U-shaped including a pair of legs connected by a rear plate. The expansion cap is urged, normally by a bolt threaded to the rear plate to wedge between and, thus, separate the free or anterior ends of the legs to a desired angular configuration.

The cage unit is fenestrated and hollow, to receive a packed, harvested bone graft or bone substitute material. Alternatively, the connecting bolt may be fixed to the rear of the cage unit and the cap driven by rotating a nut on the bolt. The cage unit and expansion cap may be configured for self-locking engagement. The expansion cap may also include anterior upper and lower horizontal bone supporting structure and an anterior recess. A pair of adjustable cage units is fixedly intercoupled by a recessed link. A set of caps is provided with each cap producing a different expansion so that a surgeon may select the cap best suited to provide the desired angular configuration between adjacent vertebrae. The caps are also configured to provide additional end plate support along a substantial portion of the front edge of the vertebral bodies.

OBJECTS AND ADVANTAGES OF THE INVENTION

The principal objects of the present invention are: to provide an improved method and apparatus for fusing together adjacent vertebrae; to provide such a method and apparatus for implanting an intervertebral fusion cage system for introducing a bone graft between adjacent vertebrae; to provide such a method and apparatus for implanting an intervertebral fusion cage system while maintaining or correcting the angular alignment of the vertebrae of the spine; to provide a method and apparatus for implanting an intervertebral dual cage system; to provide such a method and apparatus for adjustment of the alignment and balance of the spine in situ; to provide such a method and apparatus for especially engaging along a substantial length thereof the anterior, hard and compact bone layers of adjacent vertebral bodies; to provide such an apparatus having an intervertebral cage which is adjustable in situ; to provide such an apparatus having two such independently adjustable intervertebral cages; to provide such an apparatus having two intervertebral cages joined by a fixed link and that can be inserted non-parallel to each other (either in toe in and toe out or skew) and/or biased to provide better purchase to the overall system; to provide such an apparatus having two such intervertebral cages joined by a link which is recessed from the anterior surfaces of the adjacent vertebrae; to provide such an apparatus having a set of expansion caps that each provide a different degree of expansion to allow for variation in the angular configuration between the top and bottom of the cage or alternatively provides a cap that is adjustably coupled with the fusion cage for adjustment of the angle between facing surfaces of two vertebral bodies; to provide such an apparatus having an expansion cap and cage having structure permitting self-locking installation of the expansion cap onto the cage; to provide such an apparatus wherein the cages are round for insertion, but having caps with upper and lower generally linear support regions for engaging the anterior, more compact and hard bone layers of vertebrae; to provide such a fusion cage which includes an interior chamber for supporting a bone graft; to provide such a fusion cage having a group of modular or interchangeable caps with each cap producing a different degree of relative angulation between the top and bottom surfaces of the cage with the caps being usable sequentially and interchangeably to increase the expansion and resulting angulation until the surgeon is satisfied with the result; to provide such a fusion cage which is fenestrated to permit outgrowth of a bone graft into the surrounding vertebrae; to provide such an apparatus having an insertion tool which may be coupled with a fusion cage and uncoupled following insertion of the cage into an intervertebral region; to provide a method for using such an apparatus for implanting a cage unit between two adjacent vertebral bodies, packing the cage unit with a bone graft, coupling the cage unit with an expansion cap for forming the cage unit into a wedge having a predetermined angle associated with each cap between top and bottom surfaces thereof, and permitting the bone graft to grow and fuse the adjacent vertebral bodies together; providing such an apparatus and method which are relatively easy to use, inexpensive to produce and particularly well-suited for their intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

BRIEF DESCRIPTION OF THE DRAWINGS

FIG. 1 is a partially exploded perspective view of an anterior expandable spinal fusion cage apparatus in accordance with the present invention, illustrating a pair of cages, a pair of expansion bolts and a linked expansion cap unit.

FIG. 2 is a fragmentary front elevational view of a pair of adjacent vertebrae of a patient with the fusion cage apparatus implanted between the vertebral bodies and showing the expansion cap unit secured to the fusion cages.

FIG. 3 is a cross-sectional view of one cage and expansion cap of the apparatus, prior to final assembly with one of the bolts positioned through the illustrated expansion cap preparatory to engagement with a threaded bore in a rear wall of the cage.

FIG. 4 is a cross-sectional view similar to FIG. 3, illustrating the expansion cap in an expansion configuration in the fusion cage, taken along line 4—4 of FIG. 1.

FIG. 5 is an exploded perspective view at a reduced scale showing an insertion tool aligned with a cage unit of the invention.

FIG. 6 is a fragmentary perspective view showing the tool of FIG. 5 coupled with the cage unit and positioned in the intervertebral region between adjacent vertebrae during implantation of the cage unit, with portions of vertebra broken away to show detail thereof.

FIG. 7 is a side elevational view of a cage unit between a pair of adjacent vertebrae at a further reduced scale and showing the cage unit of FIG. 6 in place in the intervertebral space and the insertion tool uncoupled and removed.

FIG. 8 is an enlarged front elevational view of a first modified embodiment of a single implant in accordance with the invention.

FIG. 9 is a cross-sectional view of the apparatus of FIG. 8, illustrating one of a set of expansion caps secured to a fusion cage, taken along line 9—9 of FIG. 8.

FIG. 10 is an enlarged, fragmentary side elevational view of the expansion cap of FIG. 9.

FIG. 11 is a cross-sectional view of the cage of FIG. 9 coupled with a second of the set of extension caps configured to provide less anterior vertical height than the cap shown in FIG. 9.

FIG. 12 is a greatly enlarged, fragmentary side elevational view of the expansion cap of FIG. 11.

FIG. 13 is a cross-sectional view of the cage unit of FIG. 8 coupled with a third of the set of expansion caps configured to provide less anterior vertical height than the cap shown in FIG. 11.

FIG. 14 is an enlarged, fragmentary side elevational view of the expansion cap of FIG. 13.

FIG. 15 is an exploded perspective view of a second modified embodiment of a fusion cage apparatus in accordance with the invention, illustrating a cylindrical fusion cage with a fixed stud, an expansion cap, a face plate and nuts.

FIG. 16 is a cross-sectional view of the apparatus of FIG. 15, preparatory to final installation of the expansion cap with respect to the cage, taken along line 16—16 of FIG. 15.

FIG. 17 is a cross-sectional view similar to FIG. 16, illustrating vertical expansion of a front of the cage produced by installation of the expansion cap.

FIG. 18 is an exploded perspective view of a third modified embodiment of a fusion cage apparatus in accordance with the invention, illustrating a cage, an expansion cap and a bolt prior to installation.

FIG. 19 is a front elevational view on a reduced scale of the cage of FIG. 18.

FIG. 20 is a cross-sectional view of the cage of FIG. 19, taken along line 20—20 of FIG. 19.

FIG. 21 is a rear elevational view of the expansion cap of FIG. 18.

FIG. 22 is a cross-sectional view of the expansion cap, taken along line 22—22 of FIG. 18.

FIG. 25 is an enlarged exploded perspective view of a fourth modified embodiment of a fusion cage apparatus in accordance with the invention, illustrating an apparatus having a fusion cage and expansion cap configured for self-locking.

FIG. 26 is a front elevational view on a reduced scale of the cage of FIG. 25.

FIG. 27 is a cross-sectional view of the fusion cage of FIG. 25, taken along line 27—27 of FIG. 26.

FIG. 28 is a rear elevational view of the expansion cap of FIG. 25.

FIG. 29 is a cross-sectional view of the expansion cap of FIG. 25, taken along line 29—29 of FIG. 28.

FIG. 30 is a fragmentary diagrammatic view of a spinal column showing the fusion cage of FIG. 25 implanted with the expansion cap prior to expansion.

FIG. 31 is a view similar to FIG. 30, illustrating the expansion cap assembled on the cage and locking structures of the cage and expansion cap in mating engagement and with the cage expanded to form a wedge which supports the adjacent vertebrae in proper physiological alignment.

DETAILED DESCRIPTION OF THE INVENTION

Figures 23, 24:
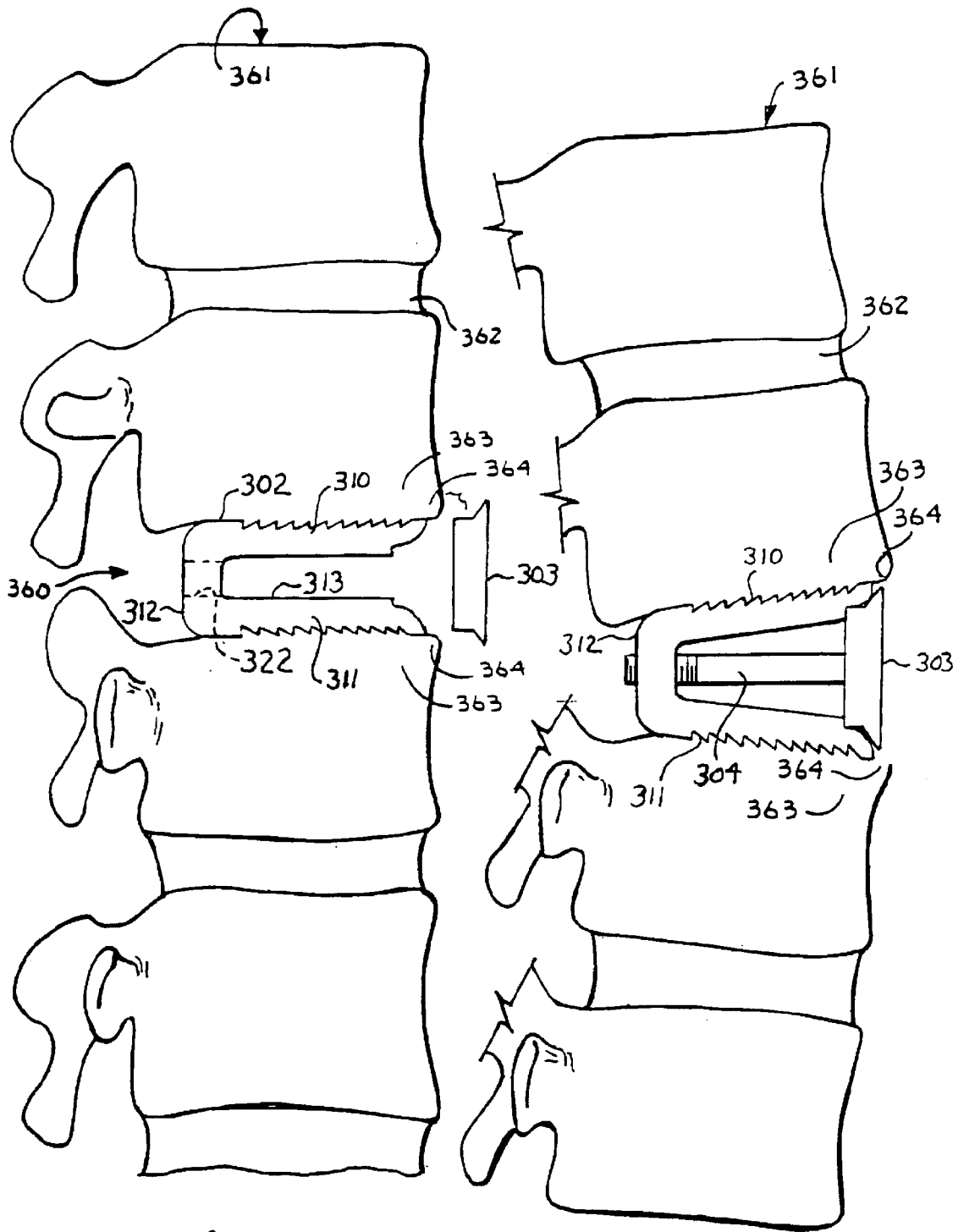
FIG. 23 is a fragmentary diagrammatic view of a spinal column showing the cage of FIG. 18 implanted with the expansion cap prior to final assembly on the cage.
FIG. 24 is a view similar to FIG. 23, illustrating the expansion cap assembled onto the cage to urge the top and bottom of the cage to form a wedge which engages the adjacent vertebrae and positions the vertebrae in proper physiological alignment.
Figure 32:
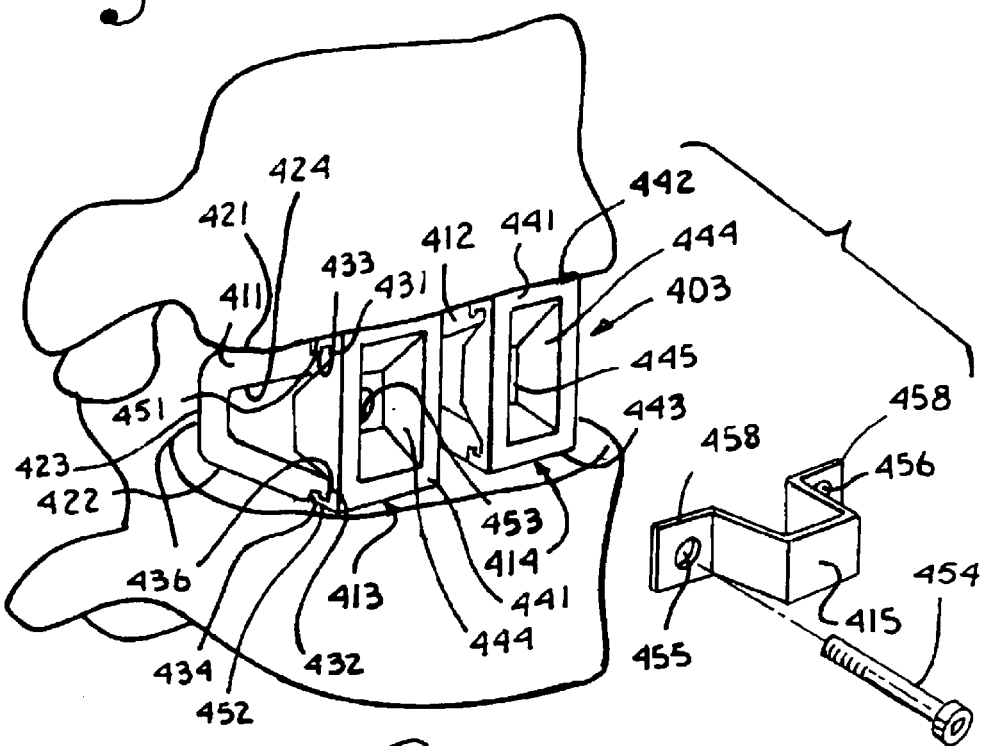
FIG. 32 is a perspective view of a pair of the implanted cages as depicted in FIG. 31, illustrating a cage link prior to assembly.
Figure 33:
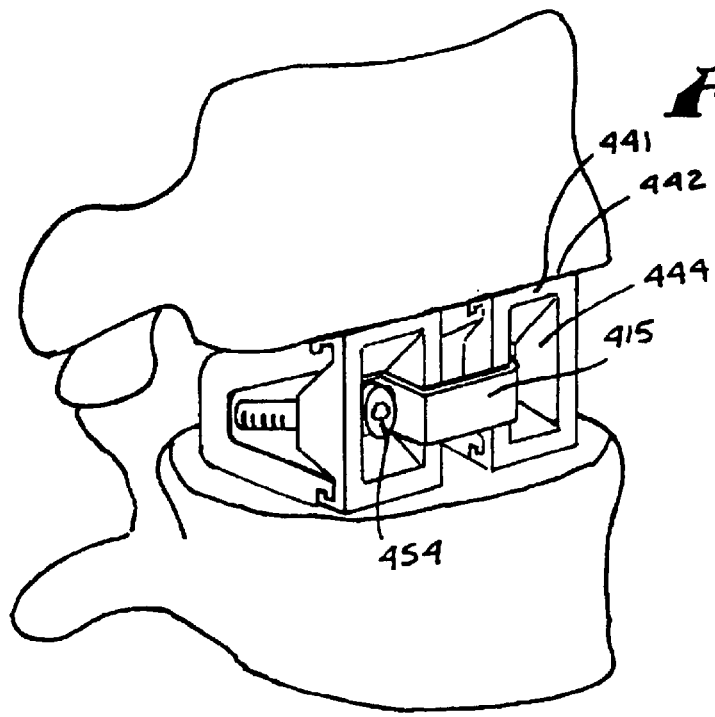
FIG. 33 is a perspective view of the cages and cage link of FIG. 32 subsequent to final assembly.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

I. Dual Cage System with Fixed Link

Referring now to the drawings, an anterior expandable spinal fusion cage system in accordance with the invention is generally indicated by the reference numeral 1 and is shown in FIGS. 1–6. An anterior view of a human spine showing the intervertebral region 2, which is the functional location of implantation of the fusion cage system 1, between upper and lower adjacent vertebral bodies or vertebrae 3 and 4, is shown in FIG. 2.

The expandible fusion cage system 1 broadly includes a pair of substantially identical, anteriorly inserted and anteriorly expandable cages or implants 10 and 11 coupled with a cap unit or expansion module 12 by a pair of set screws or bolts 13 and 14. The description "anteriorly expandable" is used to indicate that anterior ends 15 (FIG. 4) of the cages 10 and 11 are expandable rather than posterior ends 16 thereof Each of the implants 10 and 11 presents a generally truncated cylindrical overall configuration that is generally U-shaped when viewed from the side, having a horizontal central axis A extending the length thereof. An open-sided central chamber 20 is defined by a pair of spaced apart curvate top and bottom walls or legs 21 and 22, each having an outer surface 23 and 24. The walls 21 and 22 are apertured by a plurality of radial ports or windows 30, which open into the central chamber 20. The outer surfaces 23 and 24 include partial threads 31 which are interrupted by the windows 30.

The top and bottom walls 21 and 22 are coupled in spaced relationship by an enclosed rear wall, plate or web 32 having a central, threaded bore 33 and relieved corners. A front portion 34 of each of the cages 10 and 11 includes upper and lower margins 40 and 41 framing inwardly curved, upper and lower neck portions 42 and 43, each terminating at a shoulder 44 and 45. Each cage front 34 opens into an associated central chamber 20.

The cages 10 and 11 are designed with curvate or arcuate top and bottom walls 21 and 22 so that the cages 10 and 11 can be received in respective cylindrical grooves, which are predrilled into the inferior and superior surfaces, respectively of the pair of adjacent vertebral bodies 3 and 4. Those skilled in the art will appreciate that the cages may also be of a more generally rectangular configuration for implantation by tapping into the intervertebral region 2, or they may be constructed in any other geometric configuration which is suitable for implantation in an intervertebral region 2.

The expansion module 12 includes a pair of identical rectangular expansion caps or wedges 50 and 51 intercoupled in parallel alignment by a generally rectangular link 52. The link 52 is preferably recessed a distance of from about one to about five millimeters from faces 53 of the expansion caps in order to maintain an overall flush anterior profile of the implanted cage system 1. Those skilled in the art will appreciate that in certain forms the link 52 may also connect the caps 50 and 51 at a slightly convergent or divergent angle (that is the axis of the cages 10 and 11 may toe in or converge or toe out and diverge from the anterior side or may even be skewed relative to each other), such that when the cages 10 and 11 are installed at corresponding angles, the cages 10 and 11 will be more difficult to disturb and also preferably provide a slight loading or bias to the cages 10 and 11 during tightening of the caps 50 and 51 to further stabilize the intervertebral cage system 1.

The link 52 is sized to maintain the implants at a selected spacing, to enhance lateral stability and to permit a bone graft to grow from the chamber 20 outwardly, through the windows 30 and into the central portion of the intervertebral region 2, to fuse the vertebral bodies 3 and 4 together.

The expansion caps 50 and 51 each present a generally rectangular, planar face 53 having a central aperture 54, which includes a conical countersink 55 to permit flush installation of the bolts 13 and 14 having correspondingly shaped heads 62 into the caps 50 and 51. The expansion caps 50 and 51 are of unitary construction, each including a wedge 60 having a generally frustotriangular cross section coupled with a base 61 having a generally rectangular cross section. The expansion cap bases 61 are sized for insertion between the upper and lower margins 40 and 41 at the front of each of the cages 10 and 11. A beveled geometric configuration of the wedge 60 permits sliding engagement of the wedge 60 with surfaces of the necks 42 and 43 of the cages 10 and 11, which force the walls or legs 21 and 22 apart as the base 61 is snugged against the implant shoulders 44 and 45, which serve as stops.

The bolts 13 and 14 are sized and shaped to be received in the expansion cap apertures 54, with a screw head 62 received against the expansion cap countersink 55. Each screw also includes a shank 63 of reduced diameter and terminating in a threaded surface 64, which is operably received in a respective cage matingly threaded bore 33. Each screw head 62 also includes an opening 70 configured to receive a driving tool such as a wrench, screwdriver or the like (not shown).

The cages 10 and 11, expansion module 12, and bolts 13 and 14 are constructed of a strong, inert material having some elasticity such as a stainless steel or titanium alloy, although carbon fiber, porous tantalum or any other biocompatible material or combination of materials may be employed.

An insertion tool 71 for use in association with certain embodiments of the invention is depicted in FIGS. 5–7 ind includes a handle 72 coupled with a centrally bored shank portion 73 and a bolt 74 sized for registry within the bore of the shank 73. The handle 72 is centrally apertured for insertion of the bolt 74 therethrough and through the bored shank 73. The bolt 74 includes a hex type head 75 at one end and a threaded surface 76 at the opposed end. The portion of the shank 73 remote from the handle 72 is expanded to correspond to the diameter of the implant cage 10. A pair of opposed grooves 80 are machined into the expanded shank 73, leaving corresponding opposed lands 81 so that the shank 73 is sized and shaped to slidably but snuggly mate with the fusion cage 10. The lands 81 include threads 82, which correspond to the threads 31 of the top and bottom walls 21 and 22 of the cage 10.

In use, the anterior surface of a selected intervertebral region 2 of the spine of a patient is surgically exposed. The soft tissues are separated, the disc space is distracted and the disc is removed, along with any bone spurs which may be present. The spaced upper and lower vertebral bodies 3 and 4 to be stabilized and fused are then anteriorly drilled between to form a pair of opposed cage receiving grooves 84 having fixed spacing and alignment predetermined to match the alignment of the cages 10 and 11 and the spacing of the expansion module 12. One set of grooves 84 is depicted in FIG. 6, receiving one of the cages 10. Although an anterior approach is preferred, it is foreseen that a posterior, or even lateral approach could also be employed. The grooves 84 are then threaded (not shown) to correspond with the threads 31 of the cages 10 and 11.

An implant insertion tool 71 is positioned adjacent a fusion cage 10 so that the cage top and bottom walls 21 and 22 are aligned with the grooves 80 in the tool. The tool 71 and the cage 10 are urged toward each other until the cage walls 21 and 22 are received in the grooves 80 and the tool threads 83 are in registry with the implant cage threads 31, to form a continously threaded surface as shown in FIG. 6.

The bolt 74 is then inserted through the apertured handle 72 and advanced rearward until it contacts the threaded bore 33 in the rear wall of the implant 32. A driving tool such as a socket wrench (not shown) is employed to rotate the bolt 74 until the threaded surface 76 of the bolt is matingly received in the bore 33.

A user then grasps the handle 72 and positions the tool 71 and intercoupled cage 10 adjacent the intervertebral bore 84. The user rotates the handle 72 to drive the tool 71 and cage 10 into the bore 84.

When the cage 10 is properly positioned, a driving tool (not shown) is employed to rotate the bolt head 75 counter clockwise, while the cage 10 is immobilized, until the threaded surface of the bolt 76 is disengaged from the threads of the implant bore 33. The insertion tool 71 is then removed from the intervertebral bore 84 and the cage 10 remains in place. This procedure is repeated for installation of a second cage 11 at a predetermined location spaced from the first cage 10. Although the curvate outer surfaces 21 and 22 of the cages 10 and 11 are particularly well suited for such threaded insertion into a predrilled intervertebral set of grooves 84, it is foreseen that they may also be inserted either by tapping into a predrilled set of grooves 84 or by tapping directly into the distracted intervertebral region 2.

As best shown in FIGS. 3 and 4, the expansion module 12 is installed anteriorly, onto the cages 10 and 11 by alignment of the base 61 of each expansion cap 50 and 51 between a respective upper and lower cage margins 40 and 41. A respective set screw or bolt 13 or 14 is inserted through the aperture 54 of each expansion cap 50 and into the threaded bore 33 in the rear wall 32 of the cages 10 and 11.

The bolts 13 and 14 are then tightened to bring the rear surfaces of the base 61 of each expansion cap 51 into sliding engagement with the upper and lower implant neck portions 42 and 43. Continued tightening of the bolts 13 and 14 causes each base 61 to wedge the front portions of the top and bottom cage walls 20 and 21 apart, so that the cages 10 and 11 each begin to assume a generally trapezoidal shape when viewed from the side. The bolts 13 and 14 are further tightened until the rear surface of each expansion cap base 61 contacts each respective upper and lower shoulder 44 and 45, which cooperatively serve as a stop. In this manner, the shoulders 44 and 45 serve to prevent greater distraction of the disc space or region than is desired.

The expansion caps 50 and 51 are sized so that, upon coupling with the cages 10 and 11, they form a wedge which supports the vertebral bodies 3 and 4 at the proper height as well as a desired angular alignment to achieve physiological lordosis at the intervertebral region 2. While expansion caps 50 and 51 of a selected size are depicted in FIGS. 1–4, those skilled in the art will appreciate that caps producing varying degrees of expansion may be employed to produce the desired effect.

The surgeon then transplants a quantity of packed bone cells or a suitable bone substitute material or bone growth enhancer into each of the chambers 20, as well as into the area 2 between the implant cages 10 and 11. The bone cells may be introduced into the chambers 20 by a lateral approach through the open area between the top and bottom implant walls 21 and 22. Alternatively, the bone cells may be introduced into the chambers 20 by an anterior approach through the implant front 34 prior to installation of the expansion module 12 or by a combination of these methods. Bone for use in the graft may be preferably harvested from the patient as live bone, from a bone bank or from a cadaver. Demineralized bone matrix, bone morphogenic protein or any other suitable material may also be employed.

Following implantation, the bone grows between vertebrae 3 and 4 through the windows 30 with the bone in the chambers 30 and between and around the cages 10 and 11 to fuse the vertebral bodies 3 and 4 together.

II. Alternate Fusion Case System

The structure of a first modified embodiment of an anterior expandable spinal fusion cage system in accordance with the invention is shown in FIGS. 8–14 and is generally represented by the reference numeral 101. The system 101 is in many ways similar to the embodiment previously described, except the expansion caps are not joined and the cages may be fitted with expansion caps of various sizes.

In particular, the fusion cage system 101 includes a cage 102 which will normally be used in pairs between adjacent vertebrae as in the present embodiment, and a set of expansion caps, here including a large expansion cap 103, an intermediate expansion cap 104 and a small expansion cap 105, and a set screw or bolt 106. Although only three caps 103, 104 and 105 are illustrated and described in this embodiment, it is foreseen that many different caps, each producing a different decree of expansion in cage 102, may be incorporated in the set to allow the surgeon to achieve a desired degree of expansion and consequent positioning of the vertebrae relative to each other. Expansion caps are constructed of varying sizes in order to provide an implant system 101 to allow a surgeon to first try a cap producing less expansion and then, if the surgeon finds that the expansion resulting from the first cap is insufficient to produce a desired alignment between the adjacent vertebrae, to remove the first cap and insert one producing more expansion of the cage 102. The process is repeated until the desired alignment between the vertebrae is achieved. Normally the surgeon would start with the cap providing the least expansion and then larger caps in order of size, if the first is insufficient. Expansion caps 103, 104 and 105 are depicted in FIGS. 11, 12 and 14, as representative examples of a full range of possible sizes.

The cage 102 presents a generally truncated cylindrical overall configuration that is generally U-shaped when viewed from the side, including an open-sided central chamber 111, bounded by a pair of curvate top and bottom walls 112 and 113. The chamber 111 is further enclosed by a rear wall 114.

The front portion 121 of the cage 101 includes upper and lower margins 122 and 123 framing inwardly curved upper and lower neck portions 124 and 125, each portion terminating at a shoulder 131 and 132. The cage front portion 121 opens into the central chamber 111.

The large, intermediate and small expansion caps 103, 104 and 105 are of unitary construction, each including a wedge-shaped head 133 having a generally frustotriangular configuration when viewed from the side, coupled with a base 134 having a generally trapezoidal configuration. An angle A is formed by the junction of the head 133 and base 134. The size of the angle A generally conforms to the angle at the cage front 121, but the alignment varies depending upon degree of expansion of the cage 102.

The rear surface of the expansion cap head 133, which extends from base 134, slidingly engages the surfaces of the implant neck 124 and 125, forcing them apart until the base 134 rests against the shoulder stops 131 and 132.

In use, the fusion cage system 101 is implanted in a manner substantially similar to the embodiment previously described. Initially, the smallest expansion cap 105 is selected for coupling with an implant 102. The bolt 106 is then tightened until the rear surface of the expansion cap base 134 contacts the upper and lower shoulders 131 and 132 and the rear surfaces of the expansion cap head 133 rests against the upper and lower neck surfaces 124 and 125.

In the set of caps depicted, the first cap 105 produces no expansion in the anterior portion of the cage 102, but rather simply stabilizes the cage 102 where no expansion is needed. That is, the cage 102 upper wall 112 and lower wall 113 remain parallel after insertion. The surgeon then checks the alignment of the vertebrae and, if greater expansion is required, the first cap 105 is removed and the next larger cap 104 is inserted. The cap 104 causes the cage upper wall 112 and lower wall 113 to be nonparallel and wider to the front, see FIG. 11. If the surgeon is then satisfied with the alignment of the vertebrae, the cap 104 is left in place. If greater frontward expansion is required, the cap 104 is removed and the cap 103 is inserted. The cap 103 produces greater anterior expansion of the cage 102, see FIG. 9, providing a wedge-shaped configuration of the cage 102 and thus angularly realigning the vertebrae above the cage 102 relative to those below the cage 102 to cause normal physiological lordosis.

In particular, as is best shown in FIGS. 9 and 10, upon installation, the expansion caps 103 and 104 each cause the fusion cage 102 to form a generally trapezoidal configuration when viewed from the side. When used to expand, the larger the expansion cap, the greater the distance the anterior portions of the top and bottom walls 112 and 113 are wedged apart and the greater the angle associated with the intersection of planes passing through the faces of the adjacent vertebral bodies and the larger the central chamber 111 for receiving the bone graft. Thus, either by trial or by experience, the surgeon can adjust the angle of planes passing through the facing surfaces of adjacent vertebrae in situ to achieve a desired angular alignment of vertebrae for producing a desired curvature of the spine.

III. Cylindrical Fusion Case System with Fixed Screw

A second modified embodiment of an anterior expandable spinal fusion cage system in accordance with the invention is generally represented by the reference numeral 201 and is shown in FIGS. 15–17 to include an expandable implant or fusion cage 202, an expansion cap assembly 203 and a cover assembly 204. The cage 202 has a generally open-sided cylindrical configuration, having a central axis C, and upper and lower walls 210 and 211, discontinuously circumscribing a central chamber 212. Each of the walls 210 and 211 is apertured by a plurality of radially aligned windows 220. The walls 210 and 211 also each include partial threads 221, which are interspaced by the windows 220.

The cage 202 has an enclosed rear wall 222, which is perpendicularly coupled at the center with a post or stud 223. The implant 202 has upper and lower front ends 230 and 231 coupled with upper and lower axially convergent beveled surfaces 232 and 233. The front ends 230 and 231 open into the central chamber 212.

The post 223 is coaxial with axis C throughout the length of central chamber 212, and includes a shank 240, which terminates in a threaded surface 241.

The expansion cap 203 is generally frustoconical in shape and includes an axially converging circumscribing wall 242 intercoupling a rear wall 243, and an outer, radially expanded face 244. The rear wall 243 has an aperture 245 to receive the post 223. The face 244 is sized and configured for registry with the implant upper and lower front ends 230 and 231 upon installation.

The cover assembly 204 includes a generally lozenge-shaped cover plate 250 and a pair of retaining nuts 251 and 252. The cover plate 250 includes upper and lower parallel linear or planar surfaces 253 and 254 and a central, generally circular recess 255 for receiving the nut 252. The recess 255 serves to receive the nut 252 and prevent the nut 252 from projecting into the adjacent tissues, where it might cause irritation or damage. The center of the recess 255 includes an aperture 256, for receiving the post 223. It is foreseen that the cap 203 and cover assembly 204 may be manufactured as a single unit.

In use, the fusion cage 202 of the cage system 201 is inserted into a predrilled threaded set of grooves forming a bore-like structure in and between adjacent vertebral bodies and a bone graft is introduced in much the same manner as the embodiments previously described. As best shown in FIGS. 15, 16 and 17, once the cage 202 is implanted, the expansion cap 203 is positioned at the front or anterior end of the case 202 at the front ends 230 and 231, as is seen in FIG. 16, so that the expansion member or cap 203 is anteriorly located and anteriorly accessible. The expansion cap 203 is installed over the post 223, so that the rear surface of the wall 242 rests against the front end surfaces 230 and 231.

A first nut 251 is threaded onto the threaded surface of the post 241 by rotation thereof and is snugged against the rear wall of the expansion cap 243, forcing the upper and lower walls 210 and 211 apart, so that the implant cage 202 assumes the generally wedge shape depicted in FIG. 17. The nut 251 is tightened until the rearward approach of the face ring rear wall 243 is stopped by contacting the front end surfaces 230 and 231.

The cover plate 250 is installed over the expansion cap by positioning the central aperture 256 over the post 223 and threading the second nut 252 onto the threaded surface of the post 241. The nut 252 is tightened until the rear surface of the cover plate 250 is snug against the surface of the face ring 244.

Advantageously, the fusion cage system 201 is installed to a slightly inset depth between a pair of adjacent vertebrae such as partially illustrated vertebra 246, so that the cover plate upper and lower horizontal surfaces 253 and 254 provide continuous horizontal support for the harder, anterior bone margins of the adjacent vertebral bodies. In this manner, the system 201 minimizes subsidence of the cage 202 into the bone 246.

IV. Rectangular Fusion Case System with Anterior Support

A third modified embodiment 301 of an anterior expandable spinal fusion cage system in accordance with the invention is shown in FIGS. 18–24 and includes a cage implant or fusion cage 302, coupled with an expansion cap 303 by a bolt 304. The cage 302 is generally U-shaped when viewed from the side and presents a generally rectangular configuration overall, having upper, lower and rear walls 310, 311 and 312 collectively defining an open-sided central chamber 313. The walls 310 and 311 each have an outer surface 314 and 315, respectively, and include an elongate central slot 320, which extends lengthwise and opens into the central chamber 313. The outer surfaces 314 and 315 each include a series of ridges 321, which are interrupted by the slot 320.

The rear wall 312 includes a central, threaded bore 322. The cage 302 has upper and lower front ends 330 and 331 and upper and lower beveled or slanted surfaces 332 and 333.

The expansion cap 303 is generally rectangular when viewed from the front, and includes a front face 340 perpendicularly joined with generally horizontal top and bottom walls 341 and 342 and planar side walls 343. The sidewalls 343 converge inwardly and join with a generally square shaped rear wall 344, having a central bore 350. The bore 350 includes a conical countersink 351 to permit installation of the bolt 304, flush with the rear wall 344.

The bolt 304 is sized to be operably received first by the expansion cap bore 350 and then through the matingly threaded rear wall bore 322. The bolt 304 includes a head 352 and a shank 353, which terminates in a threaded surface 354. The bolt head 352 includes an opening 355 configured to receive a driving tool such as an Allen wrench (not shown).

In use, the fusion cage system 301 is installed into an intervertebral region 360 of the spine 361 of a patient as shown in FIGS. 23 and 24. Anterior exposure of the intervertebral joint 361, distraction of an affected disc 362 and preparation of the space between a pair of adjacent vertebral bodies 363 is performed as previously described.

Because the rectangular configuration of the implant cage 302 is best suited to installation by tapping into the interbody space it is not necessary to drill between the adjacent vertebral bodies 363. The implant cage 302 is inserted so that the front 323 is situated at a predetermined location which is slightly posterior to the outer bone margins 364 of the adjacent vertebral bodies 363.

The expansion cap 303 is installed anteriorly, onto the cage 302 by alignment of the sidewalls 343 between the upper and lower ends 330 and 331. The bolt 304 is aligned with and operably received in the expansion cap bore 350 as well as the fusion cage bore 322. A driving tool (not shown) is inserted into the opening 355 and employed to rotate the bolt 304 to cause the expansion cap sidewalls 343 to slidingly engage the upper and lower beveled surfaces 332 and 333 of the fusion cage 302. Continued tightening of the bolt 304 biases the implant upper and lower walls 310 and 311 apart into a wedge shape. The bolt 304 is tightened until the cap face 340 is snugged against the upper and lower ends 330 and 331 of the fusion cage 302. In this configuration, the horizontal top and bottom expansion cap walls 341 and 342 engage and abut against the outer bone margins of the vertebral bodies 364. In this manner, the top and bottom walls 341 and 342 of the expansion cap provide continuous horizontal support for the harder, anterior margin of bone 364 of the adjacent vertebral bodies 363.

It is foreseen that the cage of the present embodiment may be utilized with cages of the type shown in the previous embodiment, including a set of caps producing different expansions, caps with linear or near linear vertebra end plate support and pairs of caps that are connected together by a cross link.

V. Rectangular Fusion Cage System with Cross Link

FIGS. 25–33 illustrate a fourth modified embodiment 401 of an anterior expandable spinal fusion cage system in accordance with the invention. The structure and function of the fourth embodiment 401 is in many ways similar to that of the embodiment 301 previously described, with the major distinction being that the system incorporates a cross linking feature.

FIGS. 30 and 31 depict installation of the system 401 in a spinal column 402 having an intervertebral region 403.

The system 401 includes a pair of implant cages 411 and 412 and a pair of expansion caps 413 and 414 joined by a cross link 415. The implants 411 and 412 are similar to the implant cage 302 of the previous embodiment in that each presents a generally rectangular cross section which is best suited for installation by tapping into the intervertebral region 403.

The implant cages 411 and 412 are generally U-shaped when viewed from the side, and each includes a top wall 421, bottom wall 422, and rear wall 423, defining an open-sided central chamber 424 there between. The rear wall 423 includes a central bore 425 and the walls include a plurality of windows 426, which open into the central chamber 424.

The implants 411 and 412 include upper and lower front ends 431 and 432, which differ from those of the embodiment previously described in that each is stepped toward a channel or groove 433 and 434 formed in the top and bottom walls 421 and 422, respectively. The upper and lower front ends 431 and 432 are coupled with beveled surfaces 435 and 436.

The expansion caps 413 and 414 are of identical construction and are similar to the expansion caps of the previous embodiment in that they are generally rectangular when viewed from the front, include a front face 441, horizontal top and bottom walls 442 and 443, convergent sidewalls 444 and a rear wall 445. The expansion caps 413 and 414 differ from those previously described in that the horizontal top and bottom walls 442 and 443 each extend rearwardly to include top and bottom flanges 451 and 452 along the length thereof.

The caps 413 and 414 include in each rear wall 445 a threaded bore 453 for receiving a bolt 454, but do not include a countersink for recessing the bolt. The cross link 415 is generally U-shaped and includes a pair of apertures 455 and 456 for receiving the bolt 454 in feet 458 thereof.

The modified apparatus 401 is installed by tapping a pair of implant cages 411 and 412 into an intervertebral region 403 in a predetermined, spaced relationship. A pair of expansion caps 413 and 414 is aligned over the cages 411 and 412 in a manner similar to that of the apparatus 401 of the previous embodiment. A connector link 415 is installed in overlapping relationship between the expansion caps 413 and 414, so that each of the apertures 455 and 456 are in alignment with one of the bores 453. The apertures and aligned bores 453 receive a pair of bolts 454. Tightening advances the bolts 454 rearwardly and into the aligned bores 435 in the rear walls 423 of the cages 411 and 412. The bolts 454 are tightened until the top flanges 451 and 452 of the expansion caps 413 and 414 are received into the upper and lower implant cage channels 443 and 444, in mating engagement. In this manner, a pair of implant cages 411 and 412 are joined in spaced relationship at a predetermined angle and locked into place.

It is to be understood that while certain forms of the present invention have been illustrated and described herein, it is not to be limited to the specific forms or arrangement of parts described and shown.

What is claimed is:

1. An apparatus for positionally stabilizing adjacent vertebrae of a spine by promotion of bone fusion between the adjacent vertebrae, said apparatus comprising:
   a) an anteriorly expandable implant adapted to promote bone growth between the adjacent vertebrae; said implant having upper and lower walls extending between anterior and posterior ends of the implant and a posterior wall connecting the upper and lower walls;
   b) a post mounted in said posterior wall and extending to near the anterior end of said implant;
   c) an expansion member operably coupled with said post and engaging said upper and lower walls for operably expanding a spacing between said anterior ends of said upper and lower walls, so as to operably urge said implant upper and lower walls into a predetermined non parallel angle relative to one another and so as produce a desired alignment of the adjacent vertebrae;
   d) a cover assembly having upper and lower elongate support surfaces sized and shaped to contact and support an anterior region of the adjacent vertebrae; and
   e) a fastener mechanism operably securing said cover assembly and said expansion member to said implant during use.

2. The apparatus according to claim 1 wherein:
   a) said implant includes an interior chamber for receiving bone fragments; and
   b) said implant has a plurality of radially positioned apertures for permitting bone fragments in said chamber to join and fuse with bone in the adjacent vertebrae.

3. An apparatus for stabilizing adjacent vertebrae of a spine by promotion of bone fusion between the adjacent vertebrae, said apparatus comprising:
   a) an implant for implanting between a pair of adjacent vertebrae, said implant adapted to promote bone growth between the adjacent vertebrae;
   b) an expansion cap coupled with said implant for expanding opposite sides of an anterior end of said implant to a predetermined spacing between the sides to provide a desired alignment of the adjacent vertebrae; and
   c) an implant end cover that is non integral to said expansion cap and that is operably positioned anterior of said implant and operably secured to said implant; said cover including upper and lower support surfaces that are elongate and generally linear and that are sized and shaped to engage and operably support along a substantial anterior region of both of said adjacent vertebrae.

4. The apparatus according to claim 3 wherein:
   a) said expansion cap includes a recess for receiving a fastener to secure said cap to said implant.

5. The apparatus according to claim 3 wherein:
   a) said implant includes an interior chamber for receiving bone fragments; and
   b) said implant has a plurality of radially positioned apertures for permitting bone fragments in said chamber to join and fuse with bone in the adjacent vertebrae.

6. The apparatus according to claim 3 wherein:
   a) said expansion cap and said implant include structure for cooperatively locking together said cap and said implant when fully joined.

7. In an implant that in use is located between adjacent vertebrae for stabilizing such vertebrae and wherein the implant has upper and lower walls joined by a posterior wall, the improvement comprising:
   a) a post mounted in said posterior wall and extending to near an interior end of said implant; and
   b) an anterior expansion member coupled to said post and adapted to operably expand an anterior spacing between said upper and lower walls, as said expansion member moves posteriorly along said post during installation; said expansion member being anteriorly accessible and operably moved along said post by rotation of at least one of said expansion member and said post at said anterior end of said implant; said expansion member being sized and shaped to remain in contact with said upper and lower walls at the anterior ends of said upper and lower walls, so as to provide support to said anterior ends during usage.

8. The implant according to claim 7 including:
   a) a fastener for positioning said expansion member relative to said post and securing said expansion member to said post.

* * * * *